United States Patent
Manley

(10) Patent No.: US 12,369,787 B2
(45) Date of Patent: Jul. 29, 2025

(54) BRONCHOSCOPE TIP MARKER FOR ORIENTATION OF RADIAL ENDOBRONCHIAL ULTRASOUND PROBE

(71) Applicant: Institute For Cancer Research, Philadelphia, PA (US)

(72) Inventor: Christopher Manley, Philadelphia, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 106 days.

(21) Appl. No.: 17/799,073

(22) PCT Filed: Feb. 12, 2021

(86) PCT No.: PCT/US2021/017767
§ 371 (c)(1),
(2) Date: Aug. 11, 2022

(87) PCT Pub. No.: WO2021/163414
PCT Pub. Date: Aug. 19, 2021

(65) Prior Publication Data
US 2023/0073109 A1    Mar. 9, 2023

Related U.S. Application Data

(60) Provisional application No. 62/976,450, filed on Feb. 14, 2020.

(51) Int. Cl.
*A61B 1/267* (2006.01)
*A61B 8/00* (2006.01)
(Continued)

(52) U.S. Cl.
CPC .............. *A61B 1/2676* (2013.01); *A61B 8/12* (2013.01); *A61B 8/4416* (2013.01); *A61B 8/445* (2013.01); *A61B 10/06* (2013.01); *A61B 34/30* (2016.02)

(58) Field of Classification Search
CPC ......... A61B 8/12; A61B 8/4416; A61B 8/445; A61B 8/4461; A61B 8/4483;
(Continued)

(56) References Cited

U.S. PATENT DOCUMENTS

| 2004/0220451 A1 | 11/2004 | Gravenstein et al. |
| 2015/0126852 A1 | 5/2015 | Costello et al. |

(Continued)

FOREIGN PATENT DOCUMENTS

WO    WO-2021247744 A1 *  12/2021    ......... A61B 1/00149

OTHER PUBLICATIONS

Murgu, "Robotic assisted-bronchoscopy: technical tips and lessons learned from the initial experience with sampling peripheral lung lesions", BMC Pulmonary Medicine, 2019, 19(89), pp. 1-8.

*Primary Examiner* — Boniface N Nganga
(74) *Attorney, Agent, or Firm* — Ballard Spahr LLP

(57) ABSTRACT

A radial endobronchial ultrasound system providing localization of visualized lung lesions or nodules in the airways of a patient is provided herein. The system has three, main components: a guide sheath with a distal end, a flexible bronchoscope with a tip, and a radial endobronchial ultrasound probe. The guide sheath directs insertion of the bronchoscope into the patient, with the tip of the bronchoscope extending beyond the distal end of the guide sheath. The bronchoscope has an echogenic discrete marker formed inside and proximate its tip and a working channel configured to include and direct the probe. The probe is configured for insertion into the airways of the patient where the probe rotates to capture a 360-degree circumferential image perpendicular to the probe itself. The echogenic discrete marker on the bronchoscope provides a reference point for localization of the lung lesions or nodules visualized by the image.

11 Claims, 5 Drawing Sheets

(51) Int. Cl.
*A61B 8/12* (2006.01)
*A61B 10/06* (2006.01)
*A61B 34/30* (2016.01)

(58) Field of Classification Search
CPC ... A61B 8/4494; A61B 8/5261; A61B 1/2676; A61B 1/267; A61B 10/06; A61B 2010/045; A61B 2034/2051; A61B 2034/2072; A61B 2090/3784; A61B 2090/3925
USPC .......................................... 600/414, 424, 426
See application file for complete search history.

(56) References Cited

U.S. PATENT DOCUMENTS

| | | | |
|---|---|---|---|
| 2015/0305612 A1* | 10/2015 | Hunter | A61B 1/00057 600/109 |
| 2016/0184013 A1* | 6/2016 | Brannan | A61B 18/14 600/424 |
| 2016/0287210 A1 | 10/2016 | Chumo et al. | |
| 2018/0140359 A1 | 5/2018 | Koyrakh et al. | |
| 2018/0338676 A1 | 11/2018 | Krimsky et al. | |
| 2020/0113646 A1* | 4/2020 | Hermann | A61B 90/39 |

\* cited by examiner

BRONCHOSCOPE TIP MARKER FOR ORIENTATION OF RADIAL ENDOBRONCHIAL ULTRASOUND PROBE

FIELD

The present disclosure relates generally to bronchoscopy and, more particularly, to a radial endobronchial ultrasound probe providing better localization of visualized lung lesions.

BACKGROUND

As lung cancer screening is more readily adopted, systems and methods to diagnose and treat the disease at its earliest stage have become more critical than ever before. Peripheral pulmonary lesions or nodules are increasingly detected in patients screened for lung cancer or during disease progression of thoracic or extrathoracic malignancies. Sampling these lesions or nodules requires surgery, computed tomography (CT)-guided biopsy, or bronchoscopic procedures.

A conventional surgical technique that has been used to obtain tissue samples from central lymph nodes surrounding the lungs is known as mediastinoscopy. This procedure is performed by making an incision in the chest and inserting an instrument to extract samples. Although accurate, surgical techniques suffer from being invasive and expensive, requiring general anesthesia, and having a potential risk of infection.

One of the non-surgical techniques commonly used to stage lung cancer, which is still used today, is transbronchial needle aspiration (TBNA). This procedure is performed "blindly," meaning without real-time imaging. The pulmonologist or thoracic surgeon locates the lymph nodes only through knowledge of anatomy and images previously obtained through CT scans. This limitation makes the procedure highly operator-dependent and, therefore, diagnostic accuracy can range.

Bronchoscopic procedures are preferable to the other options because such procedures have fewer complications and are more widely applicable; often patients may not be ideal candidates for surgery or CT-guided biopsy. In addition, guidelines recommend diagnosis and staging in one single procedure. Thus, the most common interventional procedure in the field of pulmonary medicine is a bronchoscopy, in which a bronchoscope is inserted into the airways of a patient through the nose or mouth. The structure of a bronchoscope generally includes a long, thin, flexible tube that typically contains three elements: an illumination element for illuminating the region distal to the tip of the bronchoscope via an optical fiber connected to an external light source; an imaging element for returning a video image from the distal tip of the bronchoscope; and a lumen or working channel element through which instruments may be inserted. Such instruments include, but are not limited to, diagnostic instruments such as biopsy tools and therapeutic instruments such as laser, cryogenic, or RF tissue elimination probes. The distal tip of a bronchoscope can be steered or maneuvered. Rotating a handle or a component of the handle of the bronchoscope actuates a steering mechanism which moves the tip in one or more directions.

Bronchoscopies are performed by expert pulmonologists, also known as bronchoscopists, and are used routinely in the diagnosis and treatment of conditions such as lung cancer, airway stenosis, and emphysema. Bronchoscopies are typically performed by a staff of at least two caregivers: the bronchoscopist and at least one assistant, usually a nurse. During a typical procedure, the bronchoscopist holds the bronchoscope handle with one hand and the bronchoscope tube with the other hand. The bronchoscopist manipulates the distal tip of the bronchoscope inside the lung by rotating a deflection lever and by pushing and pulling the tube. Once the tip is brought to a target, a bronchoscope instrument can be inserted into the working channel to perform a diagnostic or therapeutic procedure.

Existing bronchoscopic procedures have advanced during recent years. Such procedures include electromagnetic navigation (EMN), radial endobronchial ultrasonography (R-EBUS), ultrathin bronchoscopy, and virtual bronchoscopy (VB). For purposes of example an EMN bronchoscopic system and procedure are highlighted.

FIG. 1 depicts an EMN bronchoscopy system (10) in accordance with U.S. Patent Application Publication No. 2015/0126852. The EMN system (10) is configured for planning a pathway to a target tissue (68) (planning phase) and navigating an extended working channel (80) to the target tissue (68) (navigation phase). Following navigation, surgical instruments such as those depicted in FIGS. 2A-2D, including for example, a biopsy forceps (102) (FIG. 2A), a cytology brush (104) (FIG. 2B), an aspirating needle (106) (FIG. 2C), and an ablation catheter (108) (FIG. 2D), may be inserted into the extended working channel (80) to obtain a tissue sample from the target tissue (68). The EMN system (10) generally includes an operating table (20) configured to support a patient "P"; a bronchoscope (30) configured for insertion through the mouth of the patient P and into the airways of the patient P; a monitor (40) coupled to the bronchoscope (30) for displaying video images received from the bronchoscope (30); a tracking system (50) including a tracking module (52), a plurality of reference sensors (54), and a transmitter mat (56); a computer (60) including software and/or hardware used to facilitate pathway planning, identification of the target tissue (68), and navigation to the target tissue (68); a catheter guide assembly (70) including the extended working channel (80), a locatable guide (72) that can be inserted into the extended working channel (80) and has a sensor (74) at its distal end; and a steering assembly, such as, for example, a control handle (90).

The catheter guide assembly (70) includes the control handle (90), a grip (92), and a telescopic shaft (94), which are operably connected to the extended working channel (80). By rotating the grip (92) and translating the telescopic shaft (94), the caregiver can steer the extended working channel (80) to the target tissue (68) using one hand. These movements of the control handle (90) enable the caregiver to navigate the extended working channel (80) through the tortuous path of a luminal network such as the airways of the patient P, and direct advancement of the extended working channel (80). The control handle (90) may be ergonomically shaped to facilitate grasping and/or rotation of the extended working channel (80).

As shown in FIGS. 1, 3A, and 3B, the locatable guide (72), together with the extended working channel (80), are inserted through the bronchoscope (30) and into the airways of the patient P. As a result, the locatable guide (72) and the extended working channel (80) move in concert through the bronchoscope (30) and into the airways of the patient P. Initially, the bronchoscope (30), including the extended working channel (80) and the locatable guide (72), are advanced through the mouth of the patient P and into the luminal network of the patient P. When the bronchoscope (30) is wedged and unable to advance any further through the luminal network of the patient P, the extended working channel (80) and the locatable guide (72) are advanced further without the bronchoscope (30). The extended working channel (80) and the locatable guide (72) are advanced to the target tissue (68) by translating and rotating the control handle (90).

Once the locatable guide (72) has been successfully navigated to the target tissue (68), thus completing the navigation phase, the locatable guide (72) may be removed from the extended working channel (80), leaving the extended working channel (80) in place as a guide channel for guiding surgical instruments, such as, for example, the biopsy forceps (102), the cytology brush (104), the aspirating needle (106), and the ablation catheter (108) to the target tissue (68). Before removal of the locatable guide (72) or following insertion of one or more of the surgical instruments (102), (104), (106), (108), placement may be confirmed (e.g., within and/or adjacent to the target tissue (68)) using one or more imaging modalities. For example, CT, ultrasound, fluoroscopy, and other imaging modalities may be used individually or in combination with one another.

Despite advances, the diagnostic yield of existing bronchoscopic systems and procedures remains suboptimal. Therefore, attempts have been made to meet the need for improvement to existing advanced bronchoscopic systems and procedures. One attempt is a procedure in which a diagnostic bronchoscopy is performed using a robotic platform (see, Murgu, BMP Pulmonary Medicine, 2019, 19, 89). The paper describes the procedure for performing robotic-assisted bronchoscopy (RAB) using the Monarch™ platform commercially available from Auris Health, Inc. of Redwood City, California.

SUMMARY

To meet this and other needs, and in view of its purposes, the present disclosure provides a robotic radial endobronchial ultrasound system providing localization of visualized lung lesions or nodules in the airways of a patient. The system has three, main components: a guide sheath with a distal end, a flexible bronchoscope with a tip, and a radial endobronchial ultrasound probe. The guide sheath is configured to direct the insertion of the bronchoscope into the patient, with the tip of the bronchoscope extending beyond the distal end of the guide sheath. The bronchoscope has an echogenic discrete marker formed inside and proximate its tip and a working channel configured to include and direct the radial endobronchial ultrasound probe. The radial endobronchial ultrasound probe is configured for insertion into the airways of the patient where the radial endobronchial ultrasound probe rotates to capture a 360-degree circumferential image perpendicular to the radial endobronchial ultrasound probe itself. The echogenic discrete marker on the bronchoscope provides a reference point for localization of the lung lesions or nodules visualized by the image.

It is to be understood that both the foregoing general description and the following detailed description are exemplary, but are not restrictive, of the disclosure.

BRIEF DESCRIPTION OF THE DRAWINGS

The disclosure is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DESCRIPTION OF EMBODIMENTS

Figure 1:
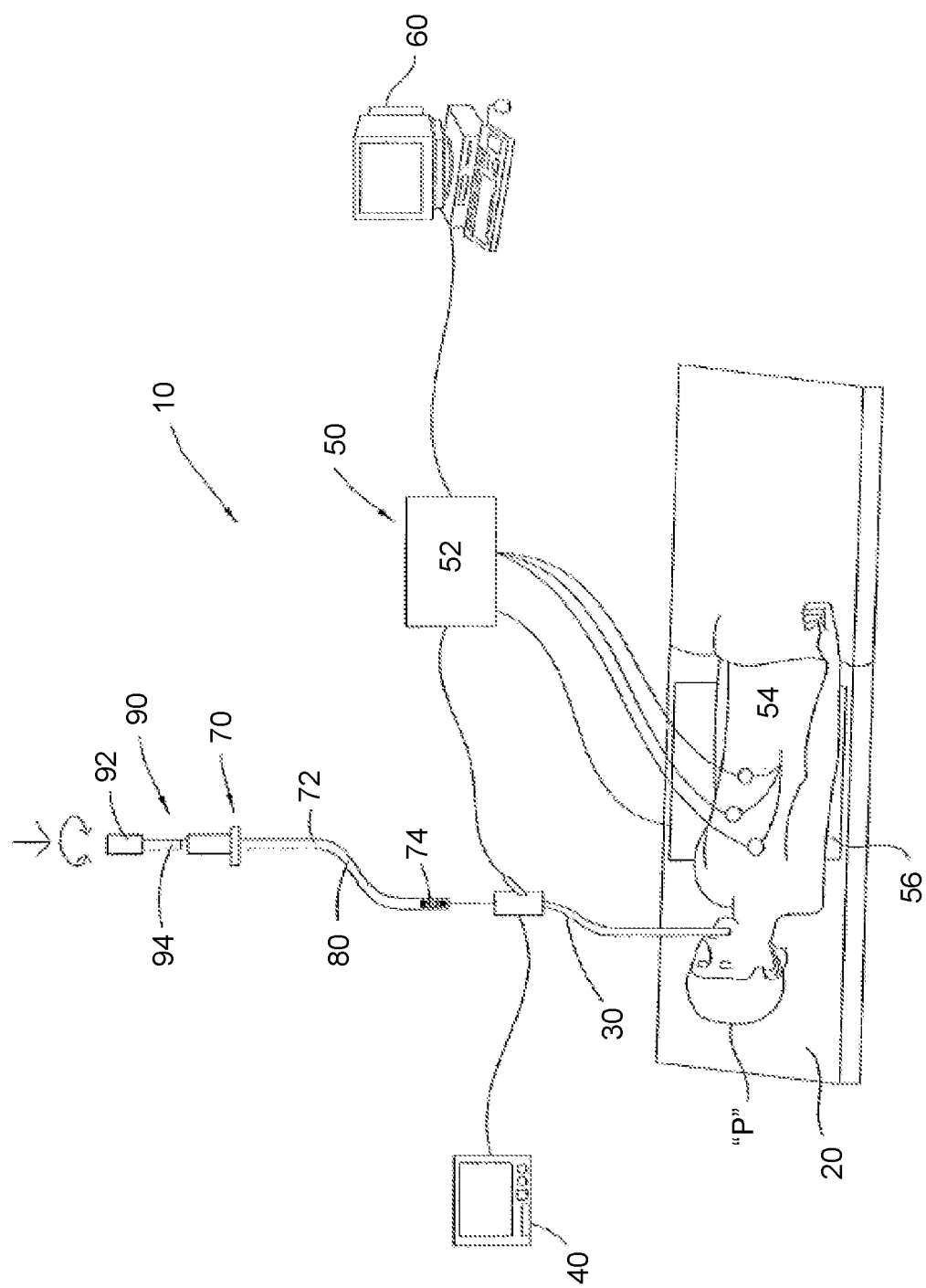
FIG. 1 depicts an electromagnetic navigation bronchoscopy system in accordance with U.S. Patent Application Publication No. 2015/0126852.
Figure 2A:
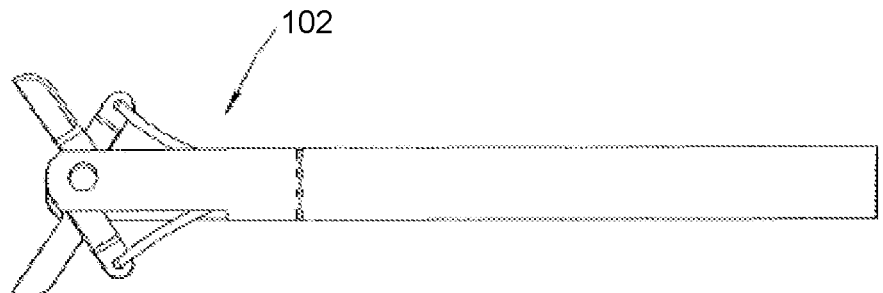
FIGS. 2A-2D are perspective views of a plurality of surgical instruments conventionally used with a bronchoscopy system.
Figure 2B:
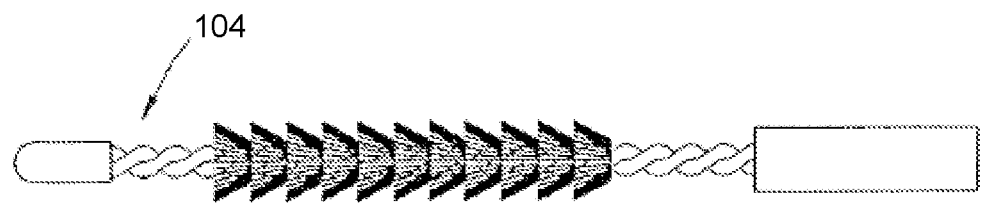
Figure 2C:
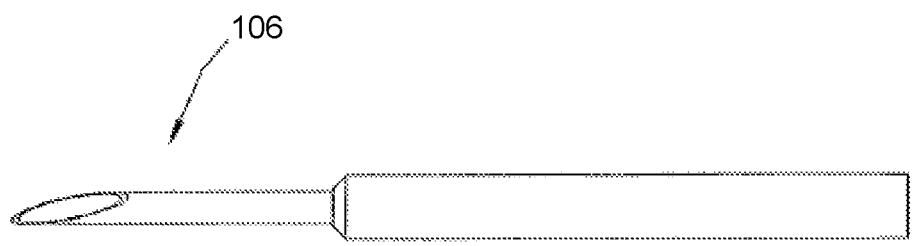
Figure 2D:
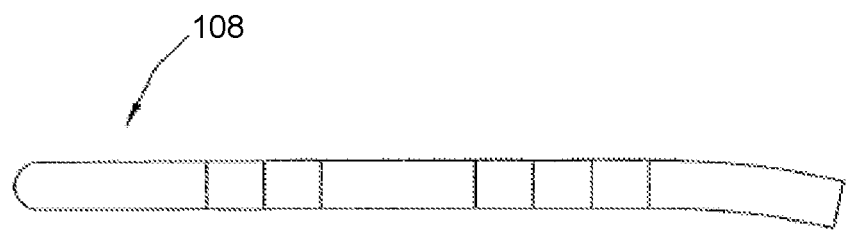
Figures 3A, 3B:
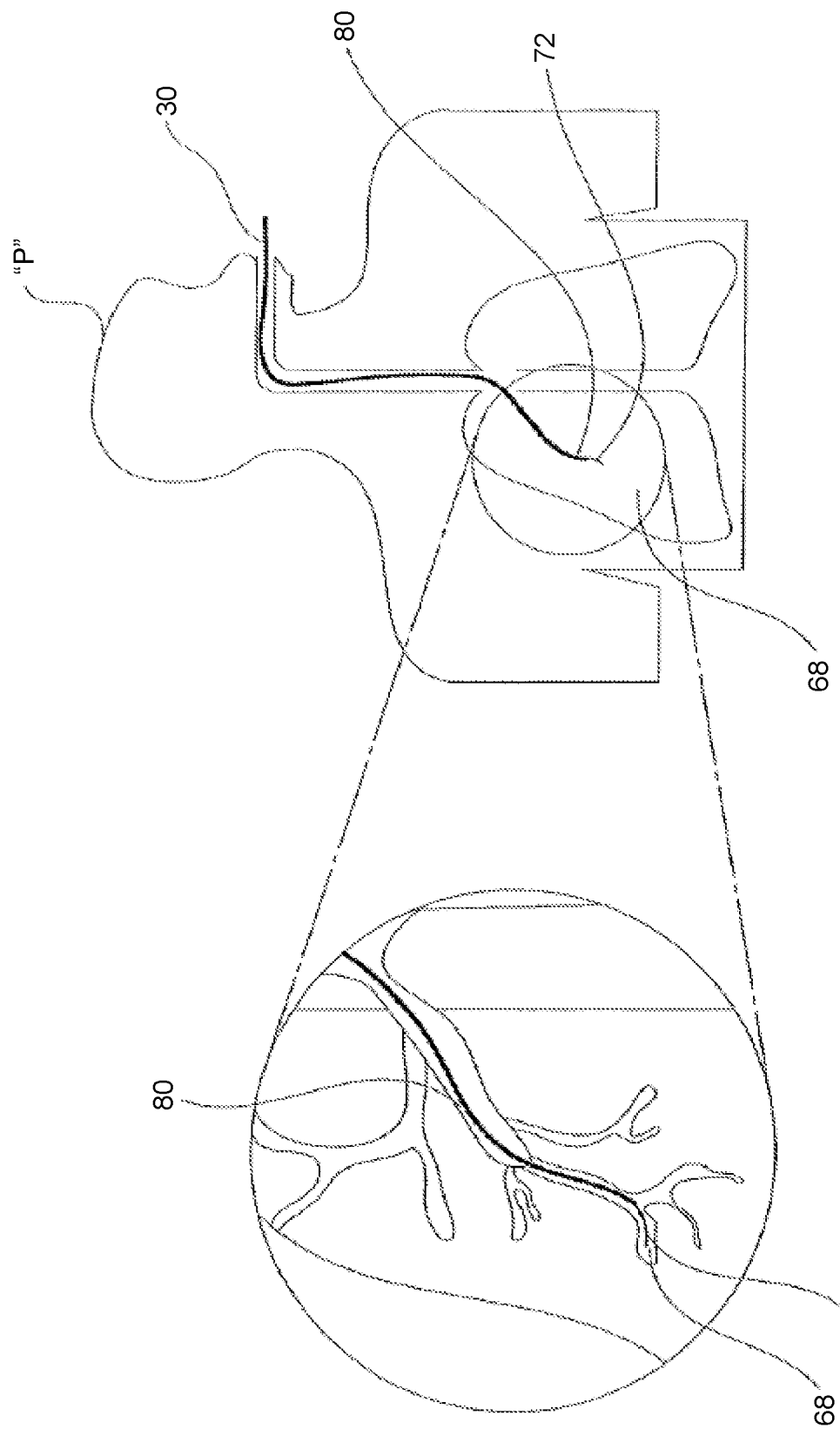
FIG. 3A is a schematic, plan view of a bronchoscope positioned within the lungs of a patient with a positioning catheter extending distally therefrom.
FIG. 3B is an enlarged area of detail of FIG. 3A, which shows bifurcations in the luminal network of the airways of a patient and the positioning catheter located in those airways.

Referring now to the drawing, in which like reference numbers refer to like elements throughout the various figures that comprise the drawing, an introduction to endobronchial ultrasound is provided. Ultrasound is a technology that uses high-frequency sound waves to create images of anatomical structures within the body of the patient P. The sound waves are sent into the body and translated into an image by the computer (60). Endobronchial ultrasound (EBUS) is ultrasound combined with endoscopy to obtain images in and around the bronchial tree or the lungs. EBUS allows the caregiver to see beyond the bronchial wall to the diseased tissue, lymph nodes, and/or lesions outside of the bronchial airways. Therefore, EBUS can be used to diagnose lung cancer, infections, and other diseases that cause enlarged lymph nodes in the chest, and to evaluate lesions that cause airway invasion. An EBUS scope also allows the caregiver to easily view difficult-to-reach areas and to access more lymph nodes for biopsy compared to conventional surgical procedures.

There are currently two imaging modalities for EBUS: radial and curvilinear (also referred to as linear or convex). The standard radial endobronchial ultrasound (R-EBUS) procedure is performed by inserting a miniature ultrasound probe (radial EBUS probe) through the working channel of a flexible bronchoscope. The caregiver moves the probe forward and backward throughout the airway. Real-time imaging of the surrounding tissue enables the caregiver to assess the internal structure of the lesion, determining the precise size, exact location, and depth of penetration of the lesion. Radial ultrasound provides a 360-degree image of the airway wall and surrounding structures external to the airway, perpendicular to the insertion direction of the bronchoscope.

Radial ultrasound also allows for a 360-degree view of the exact location of a lesion in relation to the airway. This view of the location allows for more direct and accurate sampling, increasing the diagnostic yield of the procedure. The downside to using a radial probe is that the device must be removed from the bronchoscope channel before other sampling tools can be inserted; therefore, the caregiver loses the ability to view both the bronchoscopic and ultrasound images simultaneously while performing the biopsy, which can increase the chance of missing the target site or can reduce the specimen yield. The disadvantage of radial ultrasound highlights the advantages of the EBUS scope equipped with curvilinear ultrasound.

Curvilinear ultrasound provides a 60-degree image of the airway wall and surrounding structures external to the airway, parallel to the insertion direction of the bronchoscope. Curvilinear EBUS allows caregivers to perform a technique known as transbronchial needle aspiration (TBNA) through a curvilinear EBUS bronchoscope. This bronchoscope allows for a needle to be inserted through the bronchoscope channel to biopsy lymph nodes or a suspicious lesion through the bronchial wall. The benefit of using this bronchoscope is that the needle can be viewed in real time on the video monitor, while simultaneously viewing the lymph nodes or region of interest (external to the airway) under ultrasound, enabling caregivers to more accurately guide the needle into the lymph node to obtain pathology samples. This procedure is a relatively new, minimally invasive, and safe procedure that has been proven to be highly effective in the diagnosis and staging of lung cancer.

The application of ultrasound within the lungs was first described in 1992. Ultrasound was explored as a diagnostic technique because expanding the view beyond the airways allowed caregivers to target lymph nodes more precisely, improving the diagnostic capabilities of bronchoscopy. One particular advancement was the application of EBUS-TBNA, developed to obtain diagnostic samples from lymph nodes in the central regions of the lungs, as an alternative to traditional, more invasive procedures. Thus, EBUS-TBNA was created to overcome the difficulties of traditional TBNA including low diagnostic accuracy and difficulty accessing lymph nodes.

EBUS-TBNA is performed under local anesthesia and conscious sedation in an outpatient setting. During the procedure, a special bronchoscope fitted with an ultrasound transducer and a needle is guided through the mouth and trachea of the patient to locate lymph nodes. Once the caregiver locates the lymph nodes using the ultrasound image, the caregiver can perform real-time guided needle aspiration to obtain a sample—without having to make any incisions. The sample is sent to pathology to determine the diagnosis and staging of lung cancer.

EBUS offers the advantage of simultaneously obtaining the diagnosis and stage of lung cancer in a single procedure in the outpatient setting. Using EBUS as a diagnostic tool has several benefits to the patient. The greatest benefit of using EBUS for evaluating the central airway is that the patient can potentially avoid having to undergo a more invasive surgical procedure and can eliminate the need for additional phases of testing. In addition, because EBUS is performed under conscious sedation, patients recover quickly and can generally go home the same day.

Lastly, the accuracy and speed of the EBUS procedure lends itself to rapid onsite pathologic evaluation. Pathologists can process and examine biopsy samples as they are obtained, and can request additional samples to be taken immediately if needed. This is important because the accurate diagnosis and staging of lung cancer is crucial for prognostic and therapeutic decision-making.

Figure 4:
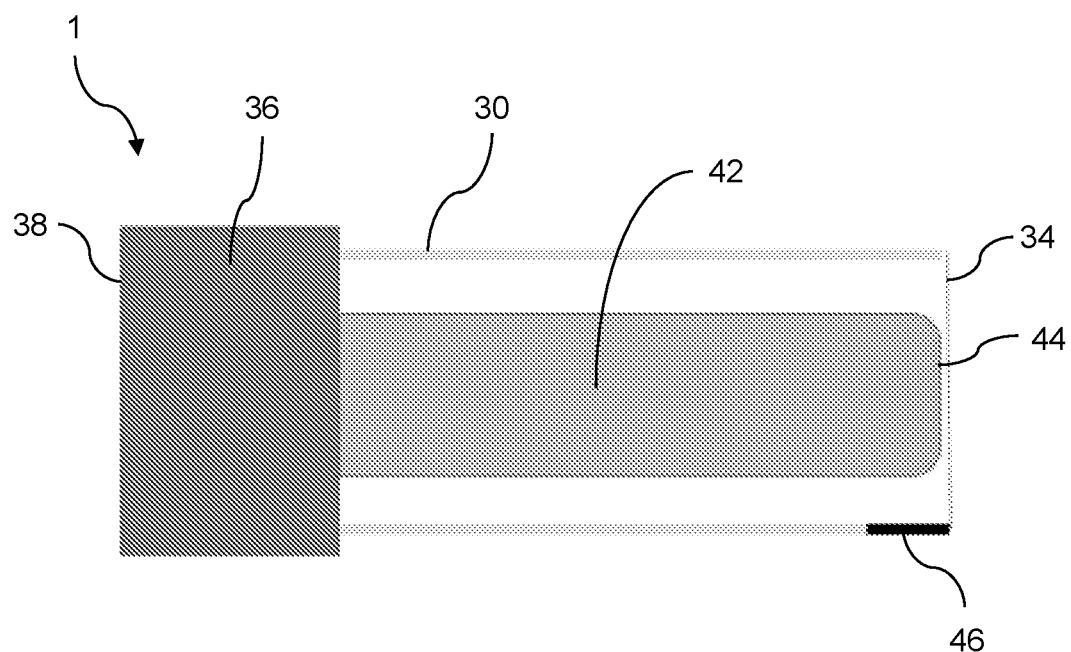
FIG. 4 illustrates in a cross-sectional view one embodiment of a robotic radial endobronchial ultrasound (R-EBUS) system according to the present disclosure.

As illustrated in FIG. 4, the present disclosure is directed specifically and preferably towards a robotic radial endobronchial ultrasound (R-EBUS) system (1) that can be used as part of the Monarch™ platform described above. The robotic system (1) includes a miniature radial EBUS probe (42) inserted into the working channel of a flexible bronchoscope (30) which is located in an outer catheter or guide sheath (36). Both the inner bronchoscope (30) and the outer guide sheath (36) have four-way steering control. That configuration allows telescoping, which enhances the stability of the bronchoscope (30) and gives the bronchoscope (30) access farther into the lung. The guide sheath (36) is typically plastic and has a proximal end (38). By "proximal" is meant the end closer and more accessible to the caregiver when the component is in use. In other words, the proximal end (38) of the guide sheath (36) is the end of the guide sheath (36) which is farther away from the location of the target tissue (68) in the patient P when in use.

The bronchoscope (30) has a distal end (34) or tip; the radial EBUS probe (42) has a distal end (44). By "distal" is the end of the bronchoscope (30) and the radial EBUS probe (42) farther away from the caregiver when these components are in use. In other words, the distal end (34) of the bronchoscope (30) and the distal end (44) of the radial EBUS probe (42) are the ends which are closer to the location of the target tissue (68) in the patient P when in use. Moreover, the distal end (34) of the bronchoscope (30) defines the exit port of the bronchoscope (30).

The R-EBUS probe (42) rotates inside the guide sheath (36). The R-EBUS probe (42) captures ultrasound images as it spins to generate a 360-degree circumferential image perpendicular to the R-EBUS probe (42) itself and is based on the echogenicity of the tissue being imaged. The goal is to advance the R-EBUS probe (42) through the working channel of the bronchoscope (30) into an airway and identify a lung lesion based on the differing echogenicity of the lesion and the air-filled lung parenchyma.

Echogenicity or echogeneity is the ability to bounce an echo, e.g., return the signal in ultrasound examinations. In other words, echogenicity is higher when the surface bouncing the sound echo reflects increased sound waves. Tissues that have higher echogenicity are called "hyperechogenic" and are usually represented with lighter colors on images in medical ultrasonography. In contrast, tissues with lower echogenicity are called "hypoechogenic" and are usually represented with darker colors. Areas that lack echogenicity are called "anechogenic" and are usually displayed as completely dark.

The challenge of imaging a nodule/lung lesion in an airway is that when the ultrasound image is captured, there is no reference point to indicate where the lesion is in relation to the bronchoscope (30). Because the R-EBUS probe (42) is spinning while capturing its image, the ultrasound image has no direction or orientation. R-EBUS probes (42) have been used in airways to localize lung lesions but the lack of directionality is an important limiting factor. For example, if the lesion appears on the left of the ultrasound image, it does not signify that the lesion is to the left of the R-EBUS probe (42).

Figure 5:
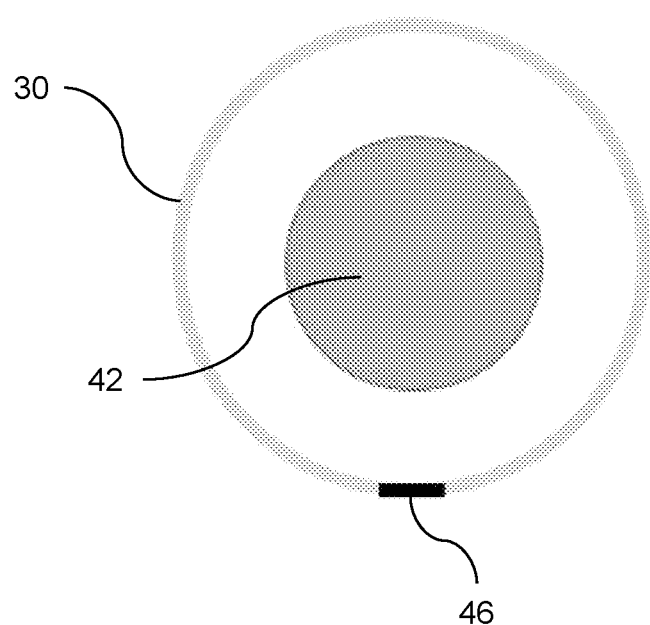
FIG. 5 is a front view of the R-EBUS probe located in the bronchoscope of the system shown in FIG. 4.
Figure 6:
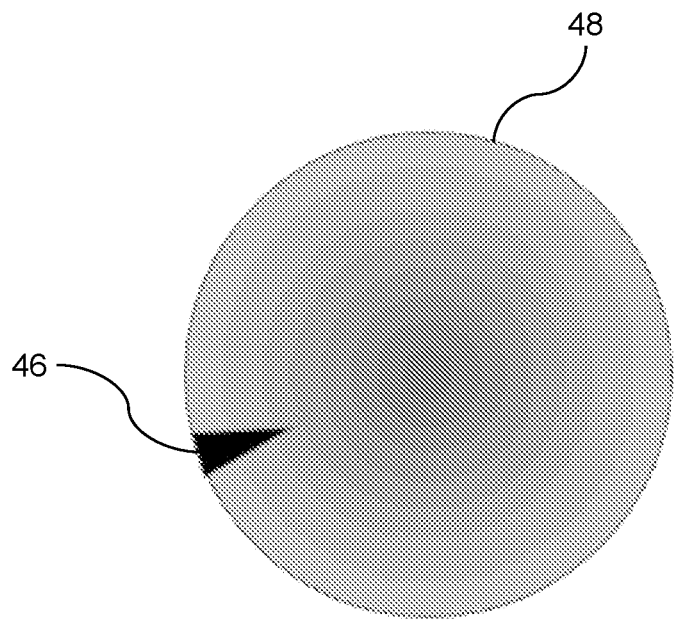
FIG. 6 shows the echogenic discrete marker of the system shown in FIGS. 4 and 5 providing a reference point on an ultrasound picture while the R-EBUS probe is inside the working channel of the bronchoscope.
Figure 7:
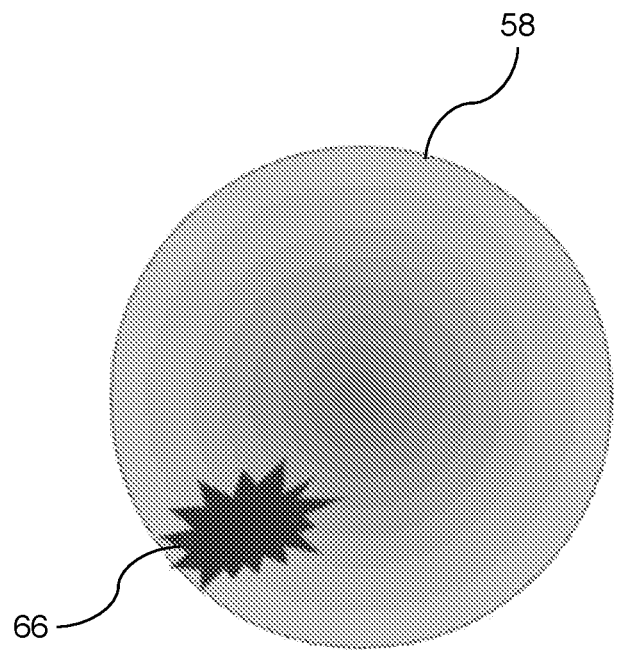
FIG. 7 illustrates how the reference point shown in FIG. 6 can be used to better localize a lung lesion or nodule on an image inside the airway of a patient.

That limitation is avoided, as shown in FIGS. 4 and 5, by placing an echogenic discrete marker (46) inside the tip or distal end (34) of the bronchoscope (30). FIG. 5 is a front view of the R-EBUS probe (42) located in the bronchoscope (30), with the echogenic discrete marker (46) in a "down" position. The distal end (34) of the bronchoscope (30) then has a uniform circumferential echogenic signal when imaged by ultrasound. As shown in FIG. 6, the echogenic discrete marker (46) provides a reference point on the ultrasound picture (48) while the R-EBUS probe (42) is inside the working channel of the bronchoscope (30). As shown in FIG. 7, this reference point can then be used to better localize a lung lesion or nodule (66) on the image (58) inside the airway of the patient P when the R-EBUS probe (42) is advanced from the working channel of the bronchoscope (30) into the airway. The echogenic discrete marker (46) provides directionality and permits orientation of the R-EBUS probe (42) for all purposes, including biopsy of the lung lesion or nodule (66).

The echogenic discrete marker (46) can be formed inside the distal end (34) of the bronchoscope (30) using any one of a number of methods known to an artisan. For example, the tip or distal end (34) of the bronchoscope (30) could be grit blasted to create the echogenic discrete marker (46). Alternatively, some of the metal around the tip or distal end (34) of the bronchoscope (30) could be abraded—perhaps using laser etching. The function of the echogenic discrete marker (46) is to induce scattering so that the feature can be identified and provide directionality. Especially in the case of an eccentric lung lesion or nodule (66), the echogenic discrete marker (46) helps the caregiver to better direct components and instruments during procedures.

The robotic R-EBUS system (1) includes as an important feature the echogenic discrete marker (46) formed inside the distal end (34) of the bronchoscope (30). That feature distinguishes the robotic R-EBUS system (1) from prior technology because known bronchoscopes have a uniform echogenic pattern when the working channel and bronchoscope tip are imaged with radial endobronchial ultrasound. Thus, the robotic R-EBUS system (1) offers the important technical advantage of providing a reference point during imaging of lung lesions by radial endobronchial ultrasound. This advantage allows the bronchoscopist, for example, to better direct a bronchoscopic biopsy needle into the lung lesion by targeting the lung lesion and avoid critical structures such as blood vessels and essential organs. The robotic R-EBUS system (1) results in better localization of lung lesions visualized by R-EBUS, minimizes bleeding from inadvertent puncture of vessels, reduces the rate of injury or damage to surrounding structures such as pneumothorax, decreases the number of biopsy attempts to obtain a diagnostic specimen, improves diagnostic yield, and shortens case duration. The robotic R-EBUS system (1) also may help provide therapeutic injections directly into lung lesions.

The echogenic discrete marker (46) can further be used to improve a standard bronchoscopy apparatus, which does not have any outer catheter or guide sheath (36). Such an apparatus includes the bronchoscope (30) having a working channel and the echogenic discrete marker (46) located inside the tip or distal end (34) of the bronchoscope (30). The R-EBUS probe (42) is located in the working channel of the bronchoscope (30) and, during the bronchoscopy procedure, is positioned in an airway. The bronchoscope (30) is steered or maneuvered into the airway and directs the R-EBUS probe (42).

The echogenic discrete marker (46) can still further be used to improve alternative R-EBUS devices. For example, the R-EBUS probe (42) can be located in (i.e., can pass through) the guide sheath (36), which for this example device is not an outer catheter or guide sheath. Both the R-EBUS probe (42) and the guide sheath (36) pass through the working channel of the bronchoscope (30) (which includes the echogenic discrete marker (46)). Once the lesion (66) is located during the bronchoscopy procedure, the R-EBUS probe (42) is removed, leaving the guide sheath (36) and the bronchoscope (30) in position. Instruments can then be applied to the lesion (66) by passing them through the working channel of the bronchoscope (30).

Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A robotic radial endobronchial ultrasound system providing localization of visualized lung lesions or nodules in the airways of a patient, the system comprising: a guide sheath having a distal end, a flexible bronchoscope having a tip, and a radial endobronchial ultrasound probe wherein:
   the guide sheath is configured to direct insertion of the bronchoscope into the patient, with the tip of the bronchoscope extending beyond the distal end of the guide sheath;
   the bronchoscope has an interior surface comprising an echogenic discrete marker proximate the tip of the bronchoscope, the interior surface defining a working channel configured to include and direct the radial endobronchial ultrasound probe; and
   the radial endobronchial ultrasound probe is configured for insertion into an airway of the patient where the radial endobronchial ultrasound probe rotates to capture a 360-degree circumferential image perpendicular to the radial endobronchial ultrasound probe itself;
   wherein the echogenic discrete marker is configured to provide an echogenic signal when imaged by the radial endobronchial ultrasound probe within the bronchoscope and provide a reference point for localization of the lung lesions or nodules visualized by the image.

2. The system according to claim 1, wherein the bronchoscope has an illumination element for illuminating a region distal to the tip of the bronchoscope via an optical fiber connected to an external light source and an imaging element for returning a video image from the tip of the bronchoscope.

3. The system according to claim 1, wherein the working channel of the bronchoscope is configured to deliver an instrument to the lung lesions or nodules.

4. The system according to claim 3, wherein the instrument is selected from the group consisting of a biopsy tool, a laser probe, a cryogenic probe, and an RF tissue elimination probe.

5. The system according to claim 4, wherein the instrument is a biopsy tool.

6. The system according to claim 4, wherein the instrument is a laser probe.

7. The system according to claim 4, wherein the instrument is a cryogenic probe.

8. The system according to claim 4, wherein the instrument is an RF tissue elimination probe.

9. The system according to claim 1, wherein the echogenic discrete marker is a grit blasted discrete marker.

10. The system according to claim 1, wherein the echogenic discrete marker is a laser etched discrete marker.

11. The system according to claim 1, wherein the echogenic discrete marker is configured to provide an echogenic signal when imaged by the radial endobronchial ultrasound probe within the bronchoscope by scattering ultrasound signals generated by the radial endobronchial ultrasound probe.

\* \* \* \* \*